(12) United States Patent  
Morrison

(10) Patent No.: US 6,506,170 B2
(45) Date of Patent: Jan. 14, 2003

(54) EXAMINATION MITT

(76) Inventor: Judith A. Morrison, 651 Fabyan Rd., Indianapolis, IN (US) 46217

(*) Notice: Subject to any disclaimer, the term of this patent is extended or adjusted under 35 U.S.C. 154(b) by 2 days.

(21) Appl. No.: 09/852,553

(22) Filed: May 10, 2001

(65) Prior Publication Data

US 2002/0169389 A1 Nov. 14, 2002

(51) Int. Cl.$^7$ .............................................. A61B 5/103
(52) U.S. Cl. ...................................... 600/587; 128/95.1
(58) Field of Search ................ 600/587, 15; 128/112.1, 128/95.1; 601/138, 134, 137

(56) References Cited

U.S. PATENT DOCUMENTS

| | | | |
|---|---|---|---|
| 2,233,686 A | * | 3/1941 | Topjian ........................ 15/227 |
| 2,694,396 A | | 11/1954 | Paschal |
| 3,154,789 A | | 11/1964 | Lewis, Jr. |
| 4,088,127 A | * | 5/1978 | Clayton et al. ............. 601/134 |
| 4,135,497 A | | 1/1979 | Meyers et al. |
| 4,281,647 A | * | 8/1981 | Antypas ............... 128/DIG. 20 |
| 4,657,021 A | | 4/1987 | Perry et al. |
| 4,793,354 A | | 12/1988 | Wright et al. |
| 4,873,982 A | | 10/1989 | Morrison |
| 5,946,727 A | * | 9/1999 | Wright et al. ............ 128/112.1 |

OTHER PUBLICATIONS

*Newsweek*, Oct. 31, 1988—*Looking for Lumps*, by Matt Clark & Frank Maier, p. 77.
*Parade Magazine*, *B–D Sensability Breast Self–Examination Aid*, Nov. 28, 1999, p. 5.

\* cited by examiner

*Primary Examiner*—Willis R. Wolfe
*Assistant Examiner*—Mahmoud Gimie
(74) *Attorney, Agent, or Firm*—Woodard, Emhardt, Naughton, Moriarty & McNett LLP

(57) ABSTRACT

A mitt is made from three sheets of thin fabric arranged with first and second sheets stitched together along their edges so that facing surfaces of the two sheets slide readily over each other. A third sheet is fastened to at least one of the first two sheets, providing an opening whereby the third sheet and the second sheet form a hand-receiver pocket. Means are provided around the opening to assist in keeping the mitt on the hand after the hand is received in the pocket. The second (middle) sheet is movable-relative to the first sheet, with the facing surfaces of these two sheets readily slidable relative to each other. The other surfaces of the sheets have surfaces of a nature more inclined to stay in place on the skin of the body portion being examined and on the fingers of the examiner while moving the second sheet relative to the first sheet and looking for lumps or irregularities below the surface of the skin of the body portion being examined. Breast self-examination can be performed with the individual either standing, or resting on their back.

19 Claims, 6 Drawing Sheets

EXAMINATION MITT

BACKGROUND OF THE INVENTION

1. Field of the Invention

This invention relates generally to methods for examining body surfaces for lumps or irregularities, and more particularly to a mitt for use in self or clinical examinations of the human body to detect sub-surface irregularities.

2. Description of the Prior Art

Some prior art devices and methods for breast examination are disclosed in my U.S. Pat. No. 4,873,982, issued Oct. 17, 1989 and entitled "Examination Garment", and in some of the references cited in that patent. One device of interest and pertaining to examination is shown in U.S. Pat. No. 4,657,021 to Perry et al., and in the article "Looking for Lumps" appearing on page 77 of the Oct. 31, 1988 issue of *Newsweek Magazine*. In 1994, it came to my attention that there is a U.S. Pat. No. 4,793,354 issued Dec. 27, 1988 entitled "Touch Enhancement" as for detection of breast cancer. Since that time, a product identified as the B-D Sensibility Breast Self-Examination Aid has appeared and was described briefly in the Nov. 28, 1999 issue of *Parade Magazine* on page 5.

The garment disclosed in my above-mentioned patent is very effective for the purpose intended. But in the form shown in that patent, it is most easily used surrounding the torso. It has been found desirable to adopt something which does not require complete removal of undergarments in order to conduct the examination. Although the above-mentioned devices for examination disclosed in the '021 patent and the *Newsweek* article do not require complete removal of undergarments, they can be awkward, relatively expensive, and require both hands to use them. The present invention is addressed to such shortcomings.

SUMMARY OF THE INVENTION

A hand-mountable device for human body examination is made from three sheets of cloth, with two sheets slidable readily over each other. The third sheet is fastened to the margins of the first two along the edges of the first two sheets, providing a hand-receiver to assist in keeping the device on the hand of the examiner during examination. The facing surfaces of the first and second sheets are readily slidable relative to each other under pressure and movement by fingers of the examiner, while the other surfaces of the first and second sheets are of a nature more inclined to stay in place on the skin of the body portion being examined and on the fingers of the examiner moving the second sheet relative to the first sheet while looking for lumps or irregularities below the surface of the skin of the body portion being examined.

DESCRIPTION OF THE ILLUSTRATED EMBODIMENT

Figure 1:
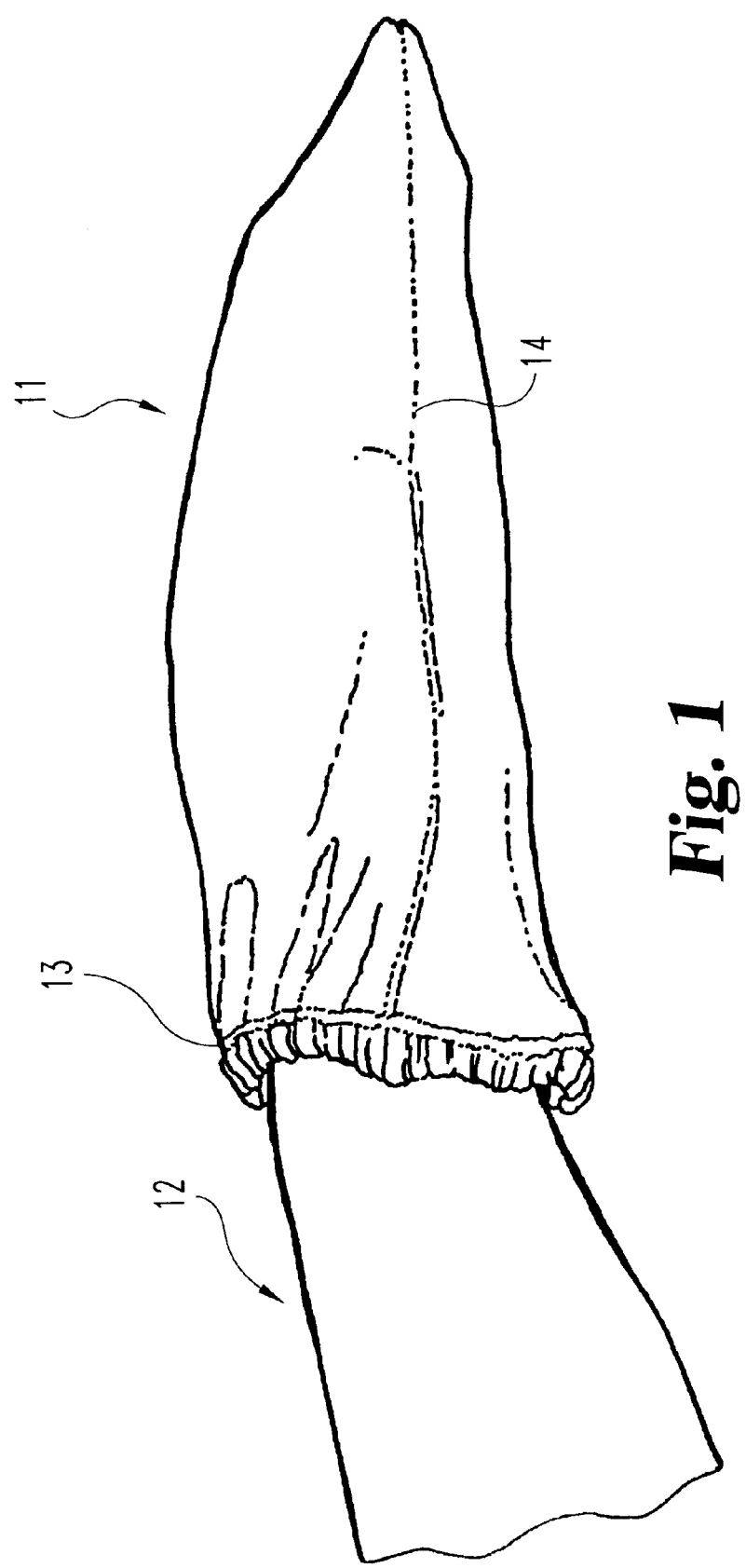
FIG. 1 is a view of the mitt worn on the hand of a person.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring now to the drawings in detail, FIG. 1 is an illustration of the examination mitt 11 received on the hand of the person's arm 12, with the hand palm-down and with the open end of the mitt pocket gathered around the arm above the wrist at 13. A stitched seam 14 can be seen and secures three sheets of fabric, as will be described.

Figure 2:
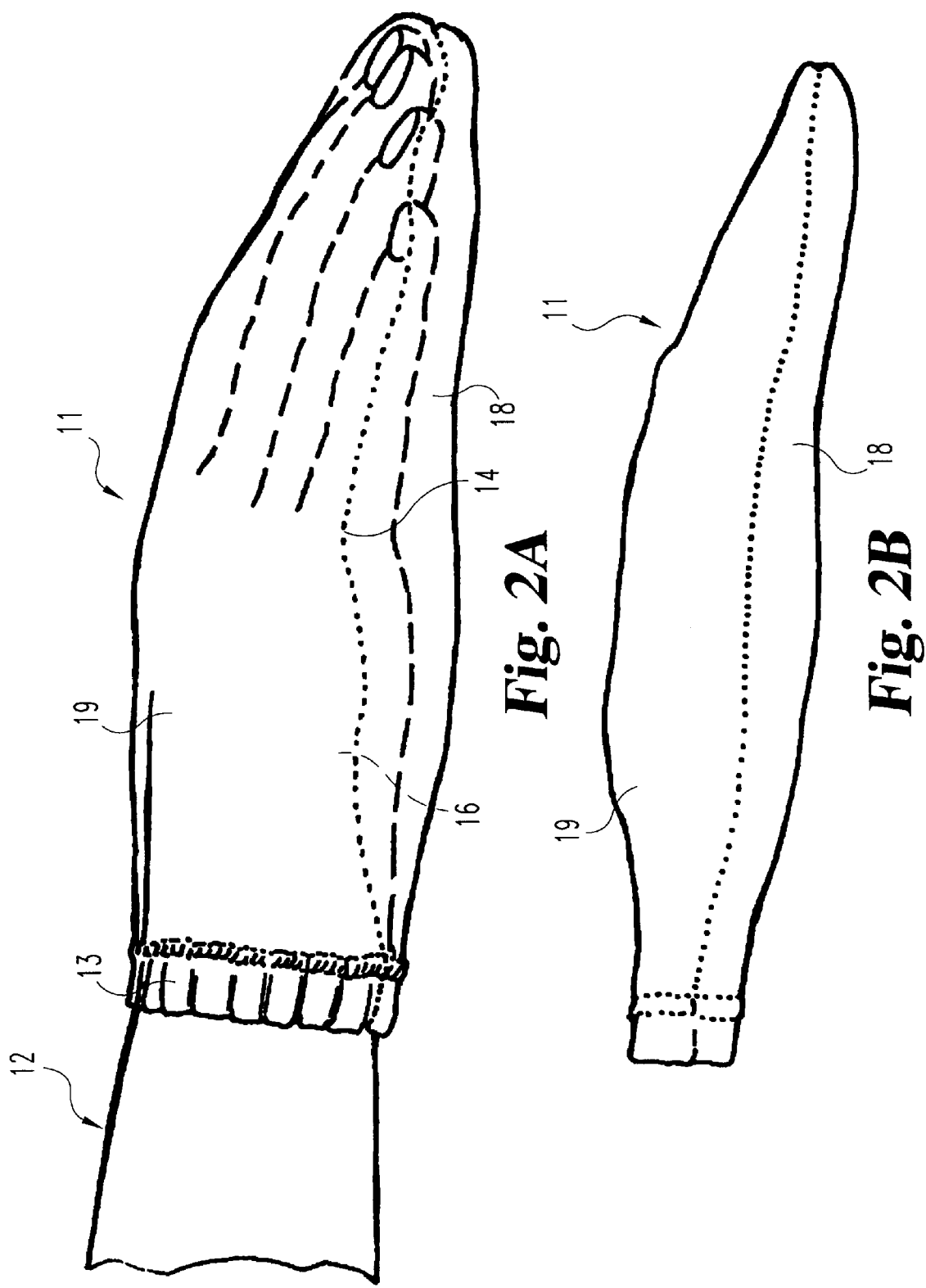
FIG. 2A is a view of the outstretched hand with the mitt receiving the hand.
FIG. 2B is a view like FIG. 2A but with the hand removed.
Figure 4A:
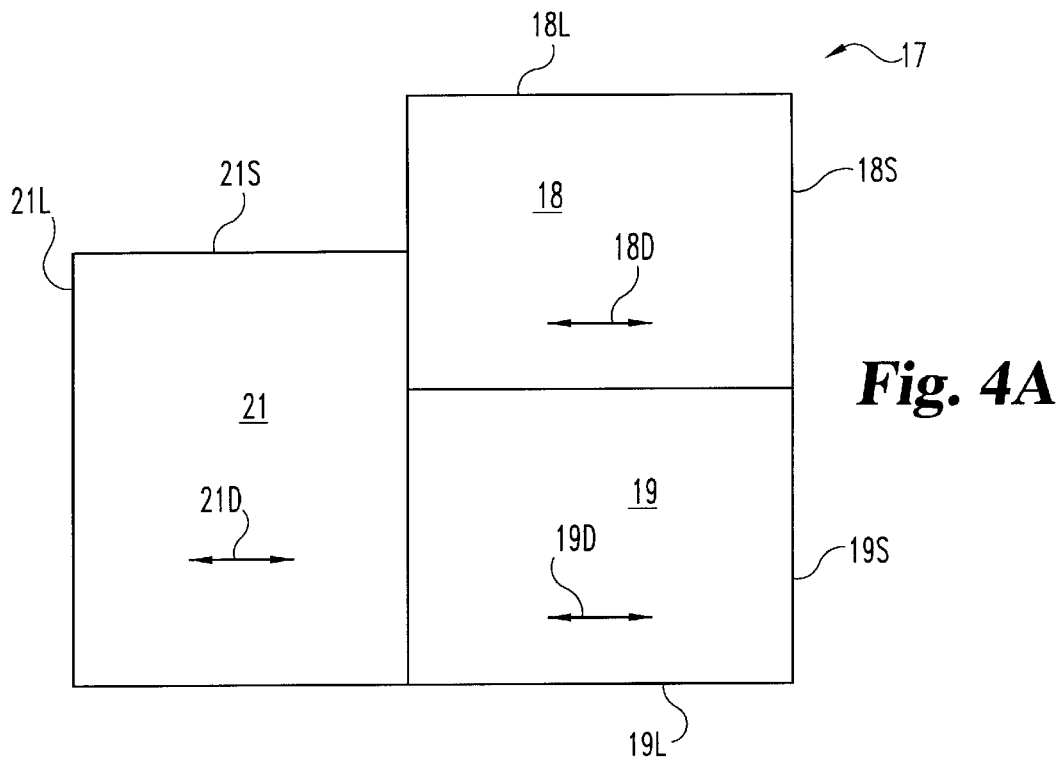
FIG. 4A is an example of a pattern of sheets from a piece of fabric.
Figure 4B:
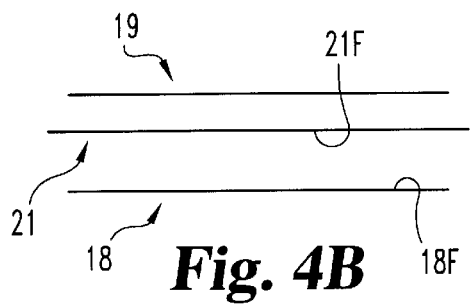
FIG. 4B is a schematic illustration of the relationship of sheet sizes.
Figure 4C:
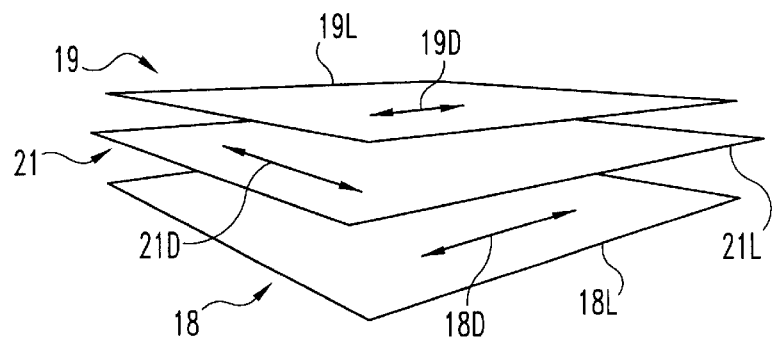
FIG. 4C is a pictorial illustration of the organization of sheets with the larger sheet between the upper and lower sheets.

FIG. 2A shows the mitt on the hand, shown in the dashed outline 16 as the mitt may be received on the hand. FIG. 2B shows the mitt as it might appear immediately after removal of the hand. As will become evident, the materials are thin and pliable enough that, when the hand is removed, the mitt can be about as thin and limp as an empty pillow slip. To facilitate construction of the mitt and referring now to FIGS. 4A, 4B and 4C, three sheets are cut from a bolt 17 of fabric and are identified as 18, 19 and 21. Fabric as disclosed in my above-mentioned patent is satisfactory for application in the present invention. The subject matter of my above-mentioned patent is incorporated herein by reference. More specifically, a cloth then known as SENSUA SOLIDS style 50690 can be used for all three plies 18, 19 and 21 of the mitt. As produced by Guilford Mills of New York, N.Y., it comprised 85% ANTRON nylon and 15% LYCRA brand spandex elastic yarn. One face of the material is relatively glossy while the other side is more dull. The material also is characterized in that it is relatively elastic in one direction (direction of dominant elasticity), while relatively inelastic in a direction perpendicular thereto.

Each of these sheets of fabric is of the same rectangular shape, sheets 18 and 19 being the same size and sheet 21 being slightly larger. As an example, sheets 18 and 19 may be 9 to 9½ inches long and 7 inches wide. Sheet 21 may be 9½ to 10 inches long, and 7⅜ to 7⅝ inches wide. Different sizes and shapes may be adopted for use depending upon preferences of the user. The important point is that the second (intermediate) sheet 21 be slightly larger than the first (bottom) sheet 18 so that the facing surfaces 18F and 21F (FIGS. 3 and 4B) thereof are freely slidable on each other but the middle sheet 21 not be so large that there be folds in it that would be detrimental to effective use of it.

For convenient reference purposes, the sheets will be referred to as having a long edge and a short edge. For sheet 18, the long edges are 18L and the short edges 18S.

Similarly, for sheet 19, the long edges are 19L and the short edges are 19S. For sheet 21, the long edges are 21L and the short edges are 21S. In assembling the mitt these sheets are stitched together with short edges together as shown at the seam 14 which extends along the two long edges of all three of the sheets and the one short edge shown in FIG. 3 at the distal end of the mitt. The other short edge of the sheets 18 and 21 are also seamed together at the proximal end of the mitt, but not with the other short edge of sheet 19. Consequently, there is the opening provided between the proximal short edges of sheets 19 and 21 to provide the opening of the pocket into which the hand is inserted. Thus, a hem 18H is provided around the seamed proximal short edges of the sheets 18 and 21 on the palm side of the mitt. A hem 22 is provided on the unseamed short proximal edge of sheet 19 to receive an elastic band in it as shown dotted at 22 on the top side 11T of the mitt.

The elastic band is provided in the upper half of the assembly at the proximal end to assist in gathering the material of sheet 19 at that location and holding the mitt on the hand. It is not necessary on the lower half, as the material 21 itself is gathered at the proximal end, and of an elastic nature with its dominant direction of elasticity (21D, FIGS. 4A and 4C) transverse to the wrist. Also, the proximal end of the mitt does not need to tightly fit the wrist, as it can be desirable to have some movement of the hand inside the mitt as well as independent movement of the fingers within the pocket of the mitt.

Figure 3:
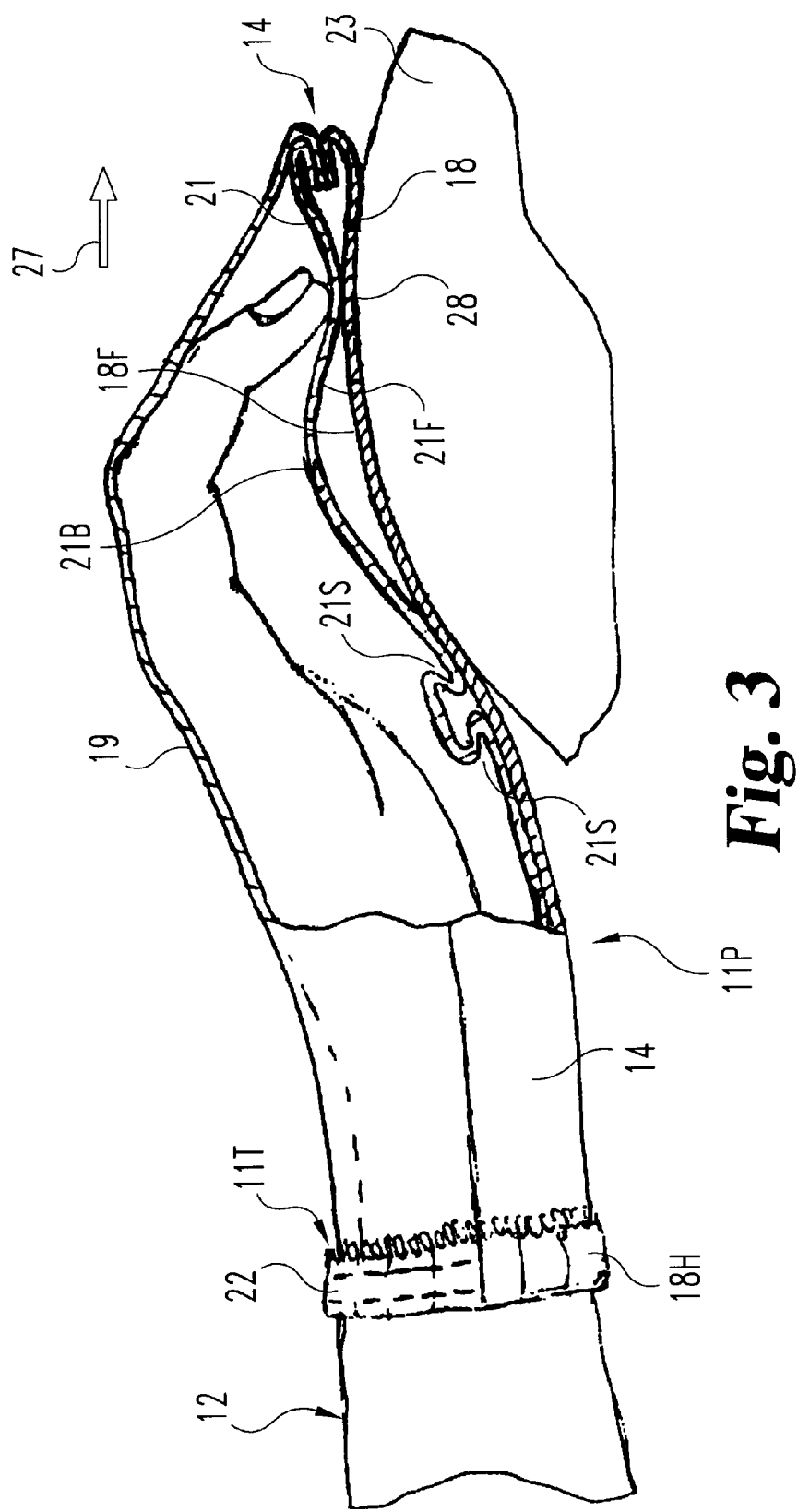
FIG. 3 is a longitudinal sectional view through the mitt with the hand in it applied to a curved surface and showing, in exaggerated form, the movement of the intermediate sheet relative to the body contact sheet.
Figure 5:
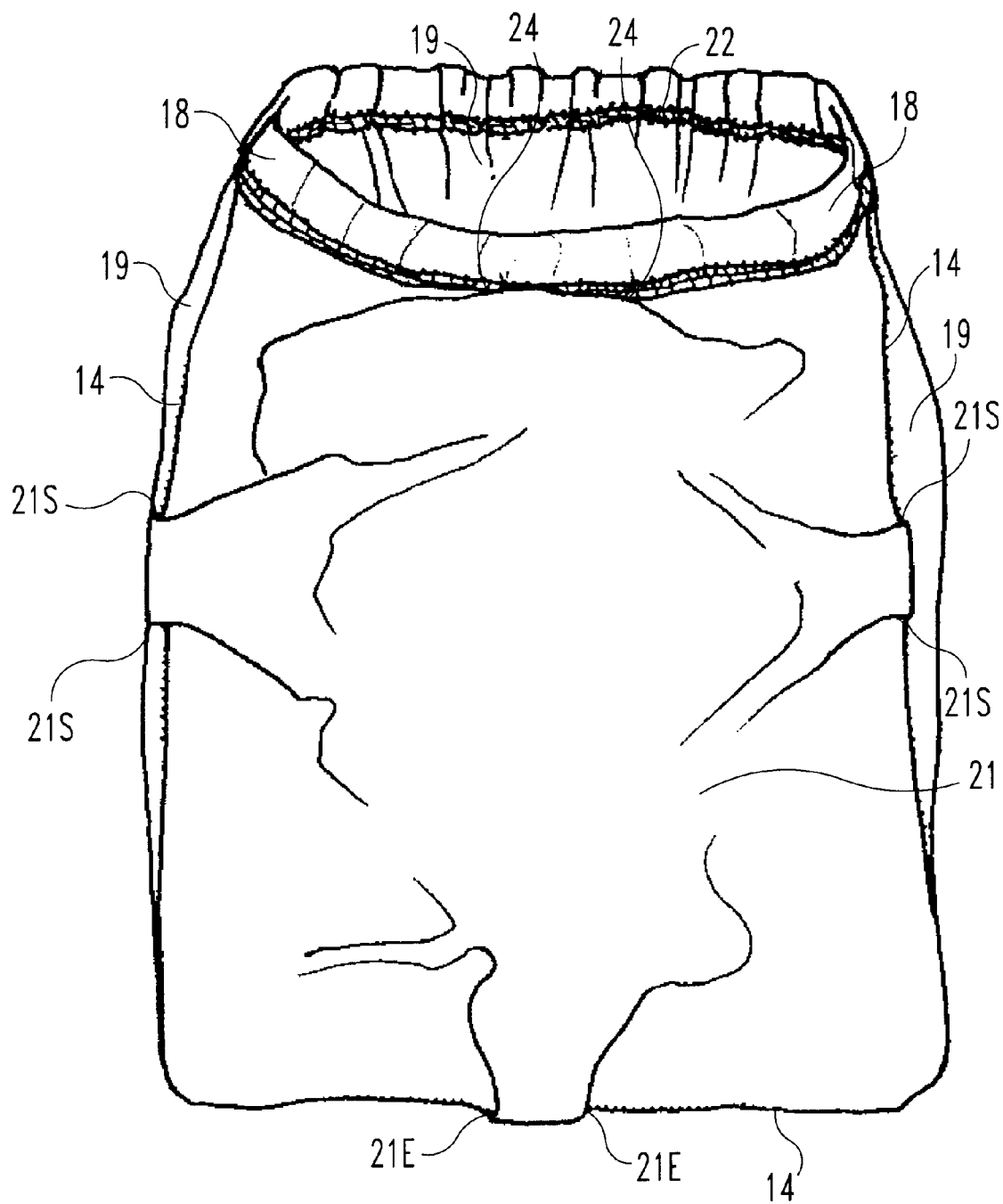
FIG. 5 is a view of the mitt turned inside-out and showing the gathering or pleating of three sides of the intermediate sheet to accommodate its greater size relative to the other two sheets.
Figure 6:
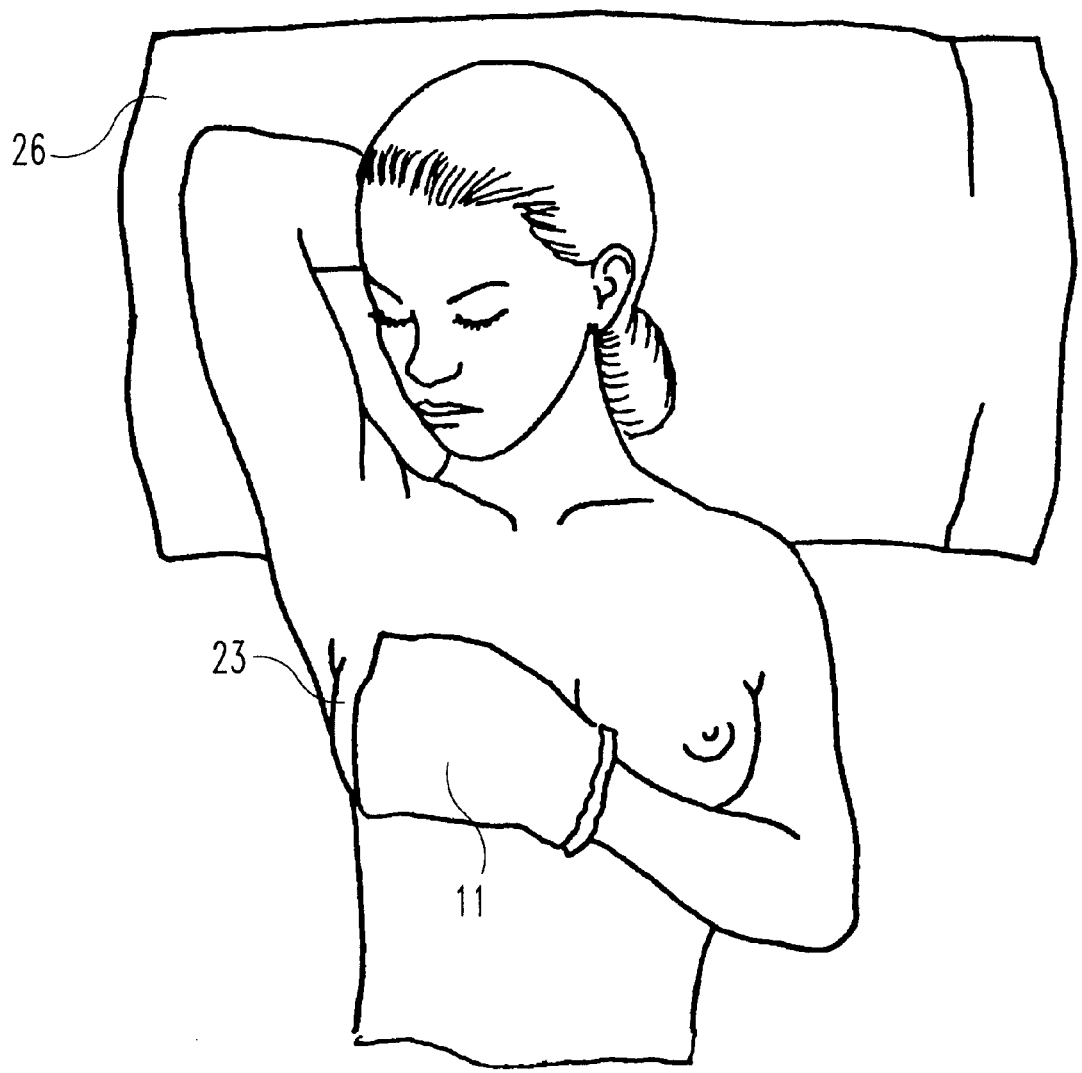
FIG. 6 is an example of the use of the mitt for self-examination by an individual lying on her back.

It has been mentioned that the second sheet is larger than the first or third sheet. Of course, this is for the purpose of enabling the fingers of the user to move the second sheet relative to the first sheet when the first sheet is placed on the breast 23 (FIGS. 3 and 6). FIGS. 3 and 5, considered together, show a preferred way to deal with assembly of the different sized sheets 18 and 21 so that there is the freedom of movement and sliding action of second sheet 21 over sheet 18, but without so much material in the second (intermediate) sheet as to cause overlapping folds in the examination area of the mitt. For this purpose, FIG. 5 shows the mitt turned inside out and sheet 21 tucked and stitched into the seam 14 at sides at 21S and at the distal end at 21E and into the cloth gathering of the two sheets 18 and 21 at the proximal end 24.

The glossy face 18F of sheet 18 is placed to be in contact with the glossy face 21F of sheet 21, and the directions of dominant elasticity to be perpendicular to one another. Therefore, when panels 18, 19 and 21 are cut from the bolt of fabric shown in FIG. 4, and sheet 18 is turned to be stitched to sheet 21, glossy sides can face each other and the directions of dominant elasticity will be perpendicular to each other. Thus, the desired relatively slippery, easy gliding faces are in touch when the assembly is made by seaming the edges at 14. For present purposes, the dominant direction of elasticity of the top sheet which is atop the pocket, does not matter but, as a matter of convenience, it will be in the same direction as 18D of sheet 18 and perpendicular to the direction for the sheet 21, which is parallel to the short edge 21S of that sheet. Thus, it is particularly convenient that all three sheets can be made from the same bolt of fabric and, when arranged in the manner shown in FIG. 4A, where the long edges of the second sheet are perpendicular to the long edges of the first and third sheets, the correct relationship of the second sheet to the first sheet is automatically established for incorporation into the mitt.

In the use of the device, the person can either be standing or reclining as shown in FIG. 6 with head on pillow 26. Since the outer face of sheet 18 is dull relative to the inner or upper face 18F, the outer face is not likely to slip on the breast, as the three middle fingers are planted on the upper (dull) surface of the inner sheet 21. Thus, it is easy to move the finger-contacting portion of inner sheet 21 toward the proximal (wrist) end relative to the outer sheet 18 as shown at the bulge 21B, for example, in FIG. 3, and then forward in the direction of arrow 27 (FIG. 3) which would flatten the bulge as the area of contact 28 is moved forward in the direction of arrow 27, without the sheet 18 slipping at all on the surface of the skin. When exploration of one breast area has been completed, the mitt may be moved in any direction to explore another area.

Also, with the mitt in any one position, all fingers can be used separately or simultaneously, as desired to achieve the benefits of the easy sliding of the sheet 21 on sheet 18 and the flexibility of the entire mitt so that if the fingers are retracted significantly in the direction opposite arrow 27, the distal end of the mitt can raise from the breast to the extent necessary for the sliding action of sheet 21 on sheet 18 to occur, and yet return to original position as the fingers are again moved forward in the direction of arrow 27. Also, the fingers, of course, can move sideways within the mitt as well as forward and backward. While the thumb and all fingers may be used, it is preferable that the distal end pads of the three middle fingers be used for the examination.

Materials and sizes other than those mentioned above, can be used, and the product can be readily laundered. Means other than stitching, for assembling the sheets, may be used. Adhesive or heat bonding seem possible. Also, although a mitten is usually considered to have a thumb feature, and that could be done in implementing the present invention, it is not necessary as indicated by the foregoing description of the preferred embodiment.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

The invention claimed is:

1. A touch-sensitive living-body examination mitt comprising:

first, second and third sheets of fabric, each sheet having a perimeter edge, the second sheet having the same shape as the first sheet, but larger than the sheet and directly contacting the first sheet; and the sheets being in overlying relationship, with marginal portions at the perimeter edges of the first and second sheets being secured together around the entire perimeter of the first and second sheets, and the marginal portion at the perimeter edge of the third sheet being secured together around the entire periphery of the first and second sheets, and the marginal portion at the perimeter edge of the third sheet being secured to the marginal portions of the first and second sheets around part of the perimeter edges of the sheets and forming a pocket between said third sheet and said second sheet, the pocket being open at one marginal portion of the third sheet to admit the hand of an examiner.

2. The device of claim 1 and wherein:

the sheets are rectangular in shape and are arranged with the second sheet pleated on the marginal portion of said second sheet in at least one location where it is secured to the first sheet.

3. The device of claim 1 and wherein:

surfaces of said first and second sheets face each other and are arranged to glide easily over each other so that effective tactile examination may be conducted of an area of a body to be examined.

4. The device of claim 3 and wherein:

the fabric of said first sheet on the facing surface has more gloss than the other surface of said first sheet.

5. The device of claim 4 and wherein:

the device has a proximal end and a distal end;

said sheets are rectangular; and the first sheet has a direction of dominant elasticity oriented from the proximal end toward the distal end of the device.

6. The device of claim 5 and wherein:

said second sheet has a direction of dominant elasticity transverse to the direction of dominant elasticity of the first sheet.

7. The device of claim 6 and wherein:

the one marginal portion of the third sheet has a hem enclosing an elastic member for gathering the one marginal portion around the pocket opening to facilitate retention of the device on the hand of the examiner.

8. The device of claim 7 and wherein:

the sheets are secured by stitching.

9. A touch-sensitive living-body examination device comprising:

first and second and third plies of cloth material, the three plies being similar in shape, the second ply being located between the first and third plies, overlying outer edge portions of the three plies being secured together except along one line, the area of the second ply being greater than the area of either of the other two plies; and the area of the second ply inboard of the secured-together edge portions being movable relative to the first and third plies.

10. The device of claim 9 and wherein:

the device has a proximal end and a distal end, the second and third plies form a hand-receiver pocket at the proximal end; and the first and second plies are secured together with tucks in the second ply at locations along sides between the proximal end and the distal end.

11. The device of claim 10 and wherein:

the first and second plies are secured together with at least one tuck in the second ply at a location on the distal end of the device.

12. The device of claim 9 and wherein:

the third ply has a hem with elastic insert at the proximal end to assist retention of the device on an examiner's hand in the pocket.

13. The device of claim 9 and wherein:

the first and second plies have glossy faces and dull faces, the glossy face of the first ply facing and in contact with the glossy face of the second ply; and the first and second plies have directions of dominant elasticity, the direction of dominant elasticity of the second ply being transverse to the direction of dominant elasticity of the first ply.

14. A touch-sensitive body examination device comprising:

first and second sheets of cloth, the second sheet overlying the first sheet, with overlying outer edge portions of the sheets being secured together around the perimeters of the sheets, the area of the second sheet being greater than the area of the first sheet;

means attached to the first sheet to form a retainer to retain the device on the hand of an examiner; and the portion of the second sheet inboard of the secured-together edge portions being movable relative to the first sheet.

15. The device of claim 14 and wherein:

the first and second sheets have directions of dominant elasticity, the direction of dominant elasticity of said first sheet being different from the direction of dominant elasticity of said second sheet.

16. The device of claim 15 and wherein:

the direction of dominant elasticity of the second sheet is transverse to the direction of dominant elasticity of the first sheet.

17. The device of claim 14 and wherein:

the first and second sheets have glossy faces and dull faces, the glossy face of the first sheet facing and in contact with the glossy face of the second sheet.

18. The device of claim 17 and wherein:

the first and second sheets have directions of dominant elasticity, the direction of dominant elasticity of said first sheet being different from the direction of dominant elasticity of said second sheet.

19. The device of claim 18 and wherein:

said means to form a retainer is a third sheet of cloth secured to the first and second sheets to form a hand-receiver pocket between said second and third sheets.

* * * * *